(12) United States Patent
Chang et al.

(10) Patent No.: US 9,512,218 B2
(45) Date of Patent: Dec. 6, 2016

(54) USE OF IL-20 ANTAGONISTS FOR ALLEVIATING SPINAL CORD INJURY

(71) Applicant: National Cheng Kung University, Tainan (TW)

(72) Inventors: Ming-Shi Chang, Tainan (TW); I-Ming Jou, Tainan (TW)

(73) Assignee: National Cheng Kung University, Tainan (TW)

(*) Notice: Subject to any disclaimer, the term of this patent is extended or adjusted under 35 U.S.C. 154(b) by 80 days.

(21) Appl. No.: 14/306,693

(22) Filed: Jun. 17, 2014

(65) Prior Publication Data

US 2014/0370015 A1 Dec. 18, 2014

Related U.S. Application Data

(60) Provisional application No. 61/835,863, filed on Jun. 17, 2013.

(51) Int. Cl.
*A61K 39/395* (2006.01)
*C07K 16/24* (2006.01)
*A61K 39/00* (2006.01)

(52) U.S. Cl.
CPC ....... *C07K 16/244* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,611,705 B2 | 11/2009 | Chang |
| 7,786,274 B2 | 8/2010 | Chang |
| 7,837,994 B2 | 11/2010 | Chang |
| 8,012,478 B2 * | 9/2011 | Chang ................. C07K 16/244 424/133.1 |
| 8,206,712 B2 | 6/2012 | Chang |
| 8,454,956 B2 | 6/2013 | Chang |
| 8,597,647 B1 * | 12/2013 | Chang ............... A61K 39/3955 424/133.1 |
| 9,127,066 B2 | 9/2015 | Chang |
| 9,217,031 B2 | 12/2015 | Chang |

* cited by examiner

*Primary Examiner* — Dong Jiang
(74) *Attorney, Agent, or Firm* — Wolf, Greenfield & Sacks, P.C.

(57) ABSTRACT

Alleviating neural injury, such as spinal cord injury, in a subject (e.g., a human subject) in need of the treatment using an IL-20 antagonist, which can be an antibody that blocks a signaling pathway mediated by IL-20. Such antibodies include anti-IL-20 antibodies and anti-IL-20R antibodies that specifically block the IL-20 signaling pathway.

14 Claims, 2 Drawing Sheets

USE OF IL-20 ANTAGONISTS FOR ALLEVIATING SPINAL CORD INJURY

CROSS-REFERENCE TO RELATED APPLICATION

This application claims the benefit of the filing date of U.S. Provisional Application No. 61/835,863, filed Jun. 17, 2013. The entire contents of this referenced application are incorporated by reference herein.

BACKGROUND OF THE INVENTION

Neural injury, such spinal cord injury (SCI) is typically associated with major trauma from, e.g., motor vehicle accidents, falls, sports injuries, and violence, leading to contusion, compression, stretch, and/or laceration of the nervous system. Neural injury is not only the result of the initial trauma, but also a consequence of the cascade of cellular and molecular events occurring after the injury (Hall and Springer, *NeuroRX.* 2004: 1: 80-100). These post-injury events are referred to as the "secondary injury," which is a major determinant of final lesion extension and functional outcome.

Many preclinical studies and clinical trials for SCI aim at alleviating such secondary injury in order to decrease the effects of certain cellular and molecular events and prevent loss of neurological function (Cardotte et al., *Clin. Orthop. Relat. Res.* 2011: 469: 732-741). There remains a need to develop new approaches for treating neural injury and alleviating symptoms associated with neural injury.

SUMMARY OF THE INVENTION

The present disclosure is based on the unexpected discoveries that an anti-IL-20 antibody successfully ameliorated symptoms of spinal cord injury (SCI) and preserved neural functions in an SCI rat model.

Accordingly, one aspect of the present disclosure relates to a method for alleviating a neural injury (e.g., SCI) in a subject, the method comprising administering to a subject in need thereof (e.g., a subject such as a human patient having, suspected of having, or at risk for neural injury) an effective amount of an IL-20 antagonist. In some embodiments, the neural injury is spinal cord injury (SCI). In other embodiments, the neural injury is associated with spinal cord ischemia, a demyelinating disease, traumatic brain injury (TBI), peripheral neuropathy, or a neurodegenerative disease.

In some embodiments, the IL-20 antagonist is an antibody that inhibits a signaling pathway mediated by IL-20, such as an antibody that binds to an IL-20 protein (e.g., human IL-20) or an antibody that binds to an IL-20 receptor (e.g., human IL-20 receptor or a subunit of the receptor). Any of the antibodies used in the method described herein can be a full-length antibody or an antigen-binding fragment thereof. Alternatively, the antibody can be a human antibody, a humanized antibody, a chimeric antibody, or a single-chain antibody.

When an antibody that binds human IL-20 is used in the method described herein, it can be the monoclonal antibody mAb7E, an antigen-binding fragment thereof, or a functional variant thereof. In one example, a functional variant of mAb7E comprises the same complementary determining regions (CDRs) as mAb7E. In another example, the functional variant is a humanized antibody of mAb7E. Such a humanized antibody can comprises a heavy chain variable region ($V_H$), which comprises the amino acid sequence of SEQ ID NO:8, and a light chain variable region ($V_L$), which comprises the amino acid sequence of SEQ ID NO:12 or SEQ ID NO:13.

Alternatively, an antibody that binds a human IL-20 receptor, e.g., binds the IL-20R1 subunit, the IL-20R2 subunit, the IL-20R1/R2 complex, the IL-22R1 subunit, or the IL-22R1/IL-20R2 complex, can be used in the methods described herein. In some embodiments, the antibody binds subunit R1 of human IL-20 receptor. Such an antibody can be a full-length antibody or an antigen-binding fragment thereof. It also can be a human antibody, a humanized antibody, a chimeric antibody, or a single-chain antibody. In one example, the antibody that binds subunit R1 of the human IL-20 receptor is an antibody comprising the same $V_H$ and $V_L$ as monoclonal antibody mAb51D or mAb7GW, or a functional variant of mAb51D or mAb7GW. A functional variant can comprise the same complementary determining regions (CDRs) as mAb51D or mAb7GW. Alternatively, a functional variant can be a humanized antibody of mAb51D or mAb7GW.

The IL-20 antagonist such as any of the antibodies described herein (e.g., an anti-IL-20 antibody or an anti-IL-20R1 antibody) can be administered to the subject in an amount effective to reduce one or more symptoms associated with neural injury (e.g., SCI). In some embodiments, the IL-20 antagonist can be administered to the subject in an amount effective to suppress the loss of cortical somatosensory evoked potentials in the subject, improve motor performance of the subject, or both.

Also within the scope of this disclosure are (a) pharmaceutical compositions for use in alleviating neural injury (e.g., SCI) in a subject, the pharmaceutical composition comprising one or more of the IL-20 antagonists described herein (e.g., an antibody that inhibits the IL-20 signaling pathway such as an antibody that binds human IL-20 or human IL-20 receptor (R1, R2, or a complex thereof); and (b) uses of the just-described pharmaceutical composition in manufacturing a medicament for alleviating the neural injury.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

BRIEF DESCRIPTION OF THE SEQUENCES

Figure 1:
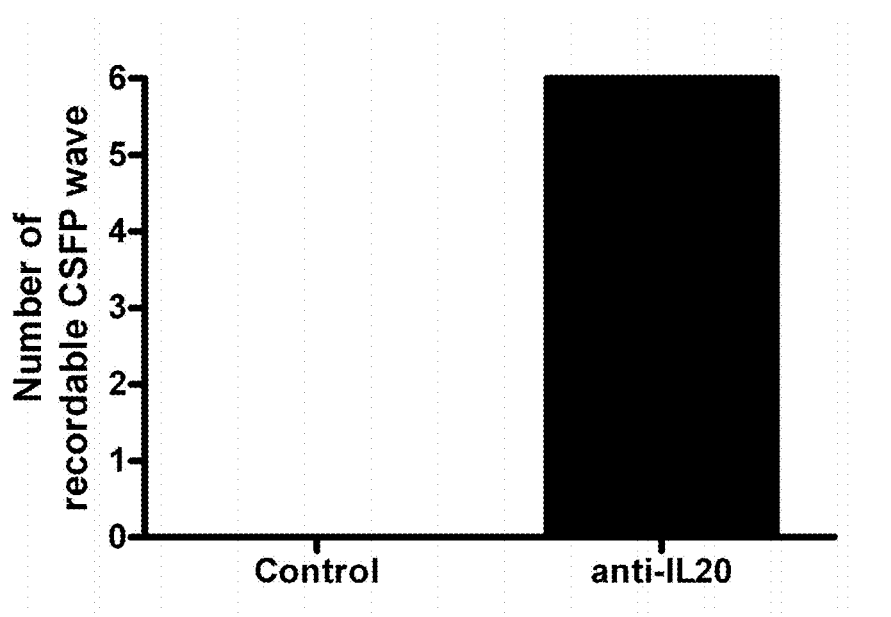
FIG. 1 is a graph showing the protective effect of anti-IL-20 antibody mAb7E on somatosensory system function following SCI in vivo, as indicated by recordable cortical somatosensory evoked potentials (CSEP). The CSEPs were recordable in SCI rats treated with the antibody (the experimental group), whereas they completely disappeared in the SCI rats treated with saline (the control group).

SEQ ID NO:1 is the nucleotide sequence encoding the heavy chain variable region of monoclonal antibody mAb7E.

SEQ ID NO:2 is the amino acid sequence of the heavy chain variable region of monoclonal antibody mAb7E.

SEQ ID NO:3 is the nucleotide sequence encoding the light chain variable region of monoclonal antibody mAb7E.

SEQ ID NO:4 is the amino acid sequence of the light chain variable region of monoclonal antibody mAb7E.

SEQ ID NO:5 is the nucleotide sequence encoding the heavy chain variable region of humanized antibodies HL1 and HL2 derived from mAb7E (precursor form, which includes a signal peptide).

SEQ ID NO:6 is the amino acid sequence of the heavy chain variable region of humanized antibodies HL1 and HL2 derived from mAb7E (precursor form, which includes a signal peptide).

SEQ ID NO:7 is the nucleotide sequence encoding the heavy chain variable region of humanized antibodies HL1 and HL2 derived from mAb7E (mature form, lacking the signal peptide).

SEQ ID NO:8 is the amino acid sequence of the heavy chain variable region of humanized antibodies HL1 and HL2 derived from mAb7E (mature form, lacking the signal peptide).

SEQ ID NO:9 is the nucleotide sequence encoding the light chain variable region of humanized antibody HL2 (precursor form, which includes a signal peptide).

SEQ ID NO:10 is the amino acid sequence of the light chain variable region of humanized antibody HL2 (precursor form, which includes a signal peptide).

SEQ ID NO:11 is the nucleotide sequence encoding the light chain variable region of humanized antibody HL2 (mature form, lacking the signal peptide).

SEQ ID NO:12 is the amino acid sequence of the light chain variable region of humanized antibody HL2 (mature form, lacking the signal peptide).

SEQ ID NO:13 is the amino acid sequence of the light chain variable region of humanized antibody HL1 (mature form, lacking the signal peptide).

SEQ ID NO:14 is the amino acid sequence of the heavy chain of monoclonal antibody mAb7GW.

SEQ ID NO:15 is the nucleotide sequence encoding the heavy chain of monoclonal antibody mAb7GW.

SEQ ID NO:16 is the amino acid sequence of the light chain of monoclonal antibody mAb7GW.

SEQ ID NO:17 is the nucleotide sequence encoding the light chain of monoclonal antibody mAb7GW.

SEQ ID NO:18 is the amino acid sequence of the heavy chain of monoclonal antibody mAb51D.

SEQ ID NO:19 is the nucleotide sequence encoding the heavy chain of monoclonal antibody mAb51D.

SEQ ID NO:20 is the amino acid sequence of the light chain of monoclonal antibody mAb51D.

SEQ ID NO:21 is the nucleotide sequence encoding the light chain of monoclonal antibody mAb51D.

DETAILED DESCRIPTION OF THE INVENTION

Injuries to the nervous system, such as brain and spinal cord injuries, are particularly devastating—often leading to lifelong disability. There is considerable evidence that the primary mechanical injury (trauma) initiates a cascade of secondary injury mechanisms that further contribute to the severity of the injury and possibly permanent neurological deficits.

The present disclosure reports the unexpected discoveries that (i) IL-20 may be involved in neural injury, for example spinal cord injury (SCI); and (ii) antibodies capable of interfering with the IL-20 signaling pathway (e.g., mAb7E) successfully alleviated symptoms of SCI in vivo and preserved neural functions. Accordingly, the present disclosure relates to methods of alleviating neural injury, such as SCI, in a subject using an effective amount of an IL-20 antagonist, which can be an antibody capable of interfering with the IL-20 signaling pathway.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

IL-20 Antagonists and Pharmaceutical Compositions Comprising Such

IL-20 is a pro-inflammatory cytokine that belongs to the IL-10 cytokine family. The IL-20 described herein refers to interleukin-20 and variants thereof that retain at least part of the activity of IL-20. As used herein, IL-20 includes all mammalian species of native sequence IL-20, including human, canine, feline, equine, or bovine. In one example, the IL-20 is a human IL-20 (GenBank accession no. NP_061194.2).

IL-20 activates the IL-20 signaling pathway via binding to IL-20 receptor, which is a dimeric complex contains subunits IL-20R1 and IL-20R2 (also known as RA and RB). Such an IL-20 receptor is shared by three functionally different cytokines, i.e., IL-19, IL-20, and IL-24, suggesting that this receptor mediates different signaling pathways dependent upon its binding to a specific cytokine. IL-20 is also capable of binding to a dimeric complex containing IL-20R2 and IL-22R1. The IL-20 receptor disclosed herein refers to one or more polypeptides that are capable of binding to and being activated by IL-20. IL-20 receptors disclosed herein include IL-20R1, IL-20R2 and IL-22R1 of any mammalian species, including, but are not limited to, human, canine, feline, equine, primate, or bovine. Examples of human IL-20 receptors include hIL-20R1 (GenBank Accession No. NM_014432.2), hIL-20R2 (GenBank Accession No. NM_144717.2) and hIL-22R1 (NM_181309.1).

Sequences of human IL-20 receptors have been described; for example, in U.S. Pat. Nos. 6,610,286; 7,122,632; 7,393,684; and 7,537,761; and U.S. Pat. App. Pub. Nos. 2006/0263850 A1; 2006/0263851 A1; 2008/0247945 A1, and 2009/0074661 A1.

The IL-20 antagonist to be used in the methods described herein is a molecule that blocks, suppresses, or reduces (including significantly) the biological activity of IL-20, including downstream pathways mediated by IL-20 signaling, such as receptor binding and/or elicitation of a cellular response to IL-20. See US2011/0064731, which is incorporated by reference herein in its entirety. The term "antagonist" implies no specific mechanism of biological action whatsoever, and is deemed to expressly include and encompass all possible pharmacological, physiological, and biochemical interactions with IL-20 whether direct or indirect. For purpose of the present disclosure, it will be explicitly understood that the term "antagonist" encompass all the previously identified terms, titles, and functional states and characteristics whereby the IL-20 itself (e.g., human IL-20), an IL-20 biological activity (including but not limited to its ability to improve functional, neurological, and motor performance outcomes in SCI), or the consequences of the biological activity, are substantially nullified, decreased, or neutralized in any meaningful degree, e.g., by at least 20%, 50%, 70%, 85%, 90%, 100%, 150%, 200%, 300%, or 500%, or by 10-fold, 20-fold, 50-fold, 100-fold, 1000-fold, or $10^4$-fold.

Exemplary IL-20 antagonists include, but are not limited to, an anti-IL-20 antibody, an anti-sense nucleic acid molecule directed to an IL-20 (including an anti-sense nucleic acid directed to a nucleic acid encoding IL-20), a small interfering RNA (siRNA) directed toward an IL-20 nucleic acid, a microRNA directed toward an IL-20 nucleic acid, an IL-20 inhibitory compound, an anti-IL-20R antibody (e.g., an antibody specifically binds IL-20R1, IL-20R2, or the dimeric complex formed thereby, IL-22R1 or the dimeric complex formed by IL-22R1/IL-20R2), an antisense nucleic acid molecule directed to a subunit of an IL-20 receptor, an siRNA or a microRNA directed to a nucleic acid encoding a subunit of an IL-20 receptor, or an IL-20R inhibitory compound. In some embodiments, an IL-20 antagonist binds IL-20 or IL-20 receptor and prevents the formation of IL-20-IL-20R complex, thereby inhibiting the IL-20 signaling pathway. In other embodiments, an IL-20 antagonist inhibits or reduces IL-20 synthesis and/or production (release). Such antagonists include antisense molecules, siRNAs and microRNAs.

Antibodies Capable of Interfering with the IL-20 Signaling Pathway

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some examples, the antibody disclosed herein specifically binds a target antigen, such as human IL-20 or one of the two subunits of a human IL-20 receptor (e.g., IL-20R1). An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to an IL-20 epitope is an antibody that binds this IL-20 epitope with greater affinity, avidity, more readily, and/or with greater duration than it binds to other IL-20 epitopes or non-IL-20 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

Antibodies capable of interfering with the IL-20 signaling pathway can be an antibody that binds an IL-20 (e.g., a human IL-20) and inhibits IL-20 biological activity and/or downstream pathways mediated by IL-20. Alternatively, such antibodies can be antibodies that bind an IL-20 receptor (IL-20R), e.g., bind to one or both of the subunits of the IL-20 receptor, and suppress the downstream signaling pathways mediated by the receptor triggered by IL-20.

(i) Anti-IL-20 Antibodies

An anti-IL-20 antibody is an antibody capable of binding to IL-20 and inhibits IL-20 biological activity and/or downstream pathway(s) mediated by IL-20 signaling. In some examples, an anti-IL-20 antibody used in the methods described herein suppresses the IL-20 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. Examples of anti-IL-20 antibodies include, but are not limited to, those disclosed in U.S. Pat. Nos. 7,435,800; 7,115,714; 7,119,175; 7,151,166; and 7,393,684; and PCT publications WO 2007/081465; WO 99/27103; WO 2004/085475; and WO 2005052000.

The binding affinity of an anti-IL-20 antibody to IL-20 (such as human IL-20) can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to IL-20 is by measuring binding affinity of monofunctional Fab fragments of the antibody. To obtain monofunctional Fab fragments, an antibody (for example, IgG) can be cleaved with papain or expressed recombinantly. The affinity of an anti-IL-20 Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human IL-20, and does not significantly bind an IL-20 from another mammalian species. In some embodiments, the antibody binds human IL-20 as well as one or more IL-20 from another mammalian species. In still other embodiments, the antibody binds IL-20 and does not significantly cross-react with other cytokines (such as the related cytokines IL-10, IL-17A, IL-19, IL-22, IL-24 and IL-26). The epitope(s) bound by the antibody can be continuous or discontinuous.

In some embodiments, the anti-IL-20 antibody described herein is anti-IL-20 antibody 7E, which refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent.

The amino acid sequences and encoding nucleotide sequences of the heavy chain variable region ($V_H$) and light chain variable region ($V_L$) of mAb7E are produced below:

```
Nucleotide sequence (SEQ ID NO: 1) and amino acid sequence
(SEQ ID NO: 2) of mAb 7E heavy chain variable region
gaa ttg aag ctt gag gag tct gga gga ggc ttg gtg cag cct gga    45
 E   L   K   L   E   E   S   G   G   G   L   V   Q   P   G    15 gga tcc atg aaa ctc tct tgt gct gcc tct gga ttc act ttt agt    90
 G   S   M   K   L   S   C   A   A   S   G   F   T   F   S    30 gac gcc tgg atg gac tgg gtc cgc cag tct cca gag aag ggg ctt   135
 D   A   W   M   D   W   V   R   Q   S   P   E   K   G   L    45 gag tgg att gct gaa att aga agc aaa gct aat aat tat gca aca   180
 E   W   I   A   E   I   R   S   K   A   N   N   Y   A   T    60 tac ttt gct gag tct gtg aaa ggg agg ttc acc atc tca aga gat   215
 Y   F   A   E   S   V   K   G   R   F   T   I   S   R   D    75
```

-continued

```
gat tcc aaa agt ggt gtc tac ctg caa atg aac aac tta aga gct 270
 D   S   K   S   G   V   Y   L   Q   M   N   N   L   R   A   90 gag gac act ggc att tat ttc tgt acc aag tta tca cta cgt tac 315
 E   D   T   G   I   Y   F   C   T   K   L   S   L   R   Y  105 tgg ttc ttc gat gtc tgg ggc gca ggg acc acg gtc acc gtc tcc 360
 W   F   F   D   V   W   G   A   G   T   T   V   T   V   S  120 tca 363
 S  121
```

Nucleotide sequence (SEQ ID NO: 3) and amino acid sequence (SEQ ID NO: 4) of mAb 7E light chain variable region

```
gat ttt gtg atg acc cag act cca ctc act ttg tcg gtt acc att  45
 D   F   V   M   T   Q   T   P   L   T   L   S   V   T   I   15 gga caa cca gcc tcc atc tct tgc aag tca agt cag agc ctc ttg  90
 G   Q   P   A   S   I   S   C   K   S   S   Q   S   L   L   30 gat agt gat gga aag aca tat ttg aat tgg ttg tta cag agg cca 135
 D   S   D   G   K   T   Y   L   N   W   L   L   Q   R   P   45 ggc cag tct cca aag cac ctc atc tat ctg gtg tct aaa ctg gac 180
 G   Q   S   P   K   H   L   I   Y   L   V   S   K   L   D   60 tct gga gtc cct gac agg ttc act ggc agt gga tca ggg acc gat 215
 S   G   V   P   D   R   F   T   G   S   G   S   G   T   D   75 ttc aca ctg aga atc agc aga gtg gag gct gag gat ttg gga gtt 270
 F   T   L   R   I   S   R   V   E   A   E   D   L   G   V   90 tat tat tgc tgg caa agt aca cat ttt ccg tgg acg ttc ggt gga 315
 Y   Y   C   W   Q   S   T   H   F   P   W   T   F   G   G  105 ggc acc aag ctg gaa atc aaa cgg 339
 G   T   K   L   E   I   K   R  113
```

A functional variant (equivalent) of mAb7E has essentially the same epitope-binding specificity as mAb7E and exhibits at least 20% (e.g., 30%, 40%, 50%, 60%, 70%, 80%, 90%, or greater) of the activity of neutralizing a signaling pathway mediated by IL-20 as relative to mAb7E. In some embodiments, a functional variant of mAb7E contains the same regions/residues responsible for antigen-binding as mAb7E, such as the same specificity-determining residues in the CDRs or the whole CDRs. The regions/residues that are responsible for antigen-binding can be identified from amino acid sequences of the heavy chain/light chain sequences of mAb7GW or mAb51D (shown below) by methods known in the art. See, e.g., www.bioinf.org.uk/abs; Almagro, J. Mol. Recognit. 17:132-143 (2004); and Chothia et al., J. Mol. Biol. 227:799-817 (1987).

In addition, determination of CDR regions in an antibody is well within the skill of the art. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

In some examples, a functional variant of mAb7E comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of mAb7E, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of mAb7E.

Alternatively, the functional variant of mAb7E comprises a $V_H$ chain at least 75% (e.g., 80%, 85%, 90%, 95%, or 98%) identical to the $V_H$ chain (mature or precursor) of mAb7E and a $V_L$ chain at least 75% (e.g., 80%, 85%, 90%, 95%, or 98%) identical to the $V_L$ chain (mature of precursor) of mAb7E.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other examples, a functional variant of mAb7E comprises a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of mAb7E, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of mAb7E.

Functional variants of mAb7E are also disclosed in U.S. Pat. No. 7,611,705 and US2011/0064731, both of which are incorporated by reference herein.

In one example, a functional variant of mAb7E is a humanized antibody derived from mAb7E. Provided below are exemplary humanized mAb7E antibodies HL1 and HL2; see also U.S. patent application Ser. No. 13/477,476:

Amino acid sequence and encoding nucleotide
sequence of the V<sub>H</sub> chain of humanized anti-IL-20
antibodies HL1 and HL2:

```
ATG TAC TTG GGA CTG AAC TAT GTT TTC ATC GTT TTT
 M   Y   L   G   L   N   Y   V   F   I   V   F

CTC CTG AAT GGT GTC CAG AGT GAA GTG CAG CTT GTG
 L   L   N   G   V   Q   S   E   V   Q   L   V

GAG TCT GGA GGA GGC TTG GTG CAG CCT GGA GGA TCC
 E   S   G   G   G   L   V   Q   P   G   G   S

CTG AAA CTC TCT TGT GCT GCC TCT GGA TTC ACT TTT
 L   K   L   S   C   A   A   S   G   F   T   F

AGT GAC GCC TGG ATG GAC TGG GTC CGC CAG GCT TCC
 S   D   A   W   M   D   W   V   R   Q   A   S

GGG AAG GGG CTT GAG TGG ATT GCT GAA ATT AGA AGC
 G   K   G   L   E   W   I   A   E   I   R   S

AAA GCT AAT AAT TAT GCA ACA TAC TTT GCT GAG TCT
 K   A   N   N   Y   A   T   Y   F   A   E   S

GTG AAA GGG AGG TTC ACC ATC TCA AGA GAT GAT TCC
 V   K   G   R   F   T   I   S   R   D   D   S

AAA AAC ACC GCC TAC CTG CAA ATG AAC AGC TTA AAA
 K   N   T   A   Y   L   Q   M   N   S   L   K

ACC GAG GAC ACT GCC GTT TAT TAC TGT ACC AAG TTA
 T   E   D   T   A   V   Y   Y   C   T   K   L

TCA CTG CGT TAC TGG TTC TTC GAT GTC TGG GGC CAG
 S   L   R   Y   W   F   F   D   V   W   G   Q

GGG ACC CTG GTC ACC GTC TCC TCA (SEQ ID NO: 5)
 G   T   L   V   T   V   S   S  (SEQ ID NO: 6)
```

The underlined region refers to the signal peptide and the boldfaced/italic regions are the CDRs. SEQ ID NOs: 8 and 7 represent the mature V<sub>H</sub> amino acid sequence (lacking the signal peptide) and its encoding nucleotide sequence, respectively.

Amino acid sequence and encoding nucleotide
sequence of the V<sub>L</sub> chain (VL2) of a humanized
anti-IL-20 antibody HL2:

```
ATG ATG AGT CCT GCC CAG TTC CTG TTT CTG TTG GTG
 M   M   S   P   A   Q   F   L   F   L   L   V

CTC TGG ATT CGG GAA ACC AAC GGT GAT ATC GTG ATG
 L   W   I   R   E   T   N   G   D   I   V   M

ACC CAG ACT CCA CTC TCT TTG TCC GTT ACC CCT GGA
 T   Q   T   P   L   S   L   S   V   T   P   G

CAA CCA GCC TCC ATC TCT TGC AAG TCA AGT CAG AGC
 Q   P   A   S   I   S   C   K   S   S   Q   S

CTC TTG GAT AGT GAT GGA AAG ACA TAT TTG AAT TGG
 L   L   D   S   D   G   K   T   Y   L   N   W

TTG TTA CAG AAG CCA GGC CAG TCT CCA CAG CAC CTC
 L   L   Q   K   P   G   Q   S   P   Q   H   L

ATC TAT CTG GTG TCT AAA CTG GAC TCT GGA GTC CCT
 I   Y   L   V   S   K   L   D   S   G   V   P

GAC AGG TTC AGT GGC AGT GGA TCA GGG ACC GAT TTC
 D   R   F   S   G   S   G   S   G   T   D   F

ACA CTG AAA ATC AGC AGA GTG GAG GCT GAG GAT GTT
 T   L   K   I   S   R   V   E   A   E   D   V

GGA GTT TAT TAT TGC TGG CAA AGT ACA CAT TTT CCC
 G   V   Y   Y   C   W   Q   S   T   H   F   P
```

-continued

```
TGG ACC TTC GGT GGA GGC ACC AAG GTG GAA ATC
 W   T   F   G   G   G   T   K   V   E   I

AAA (SEQ ID NO: 9)
 K  (SEQ ID NO: 10)
```

The underlined region refers to the signal peptide and the boldfaced/italic regions are the CDRs. SEQ ID NOs: 12 and 11 represent the mature $V_L$ amino acid sequence (lacking the signal peptide) and its encoding nucleotide sequence, respectively.

Humanized antibody HL1 comprises the same $V_H$ chain as HL2 and a $V_L$ chain (SEQ ID NO:13; mature form) that is otherwise identical to the $V_L$ of HL2 except that the I residue at position 2 of mature $V_L$ of HL2 is replaced with F.

Also disclosed herein are functional variants of the above-noted humanized antibodies HL1 and HL2. Such functional variants can comprise a $V_H$ chain that comprises an amino acid sequence at least 85% (e.g., 90%, 92%, 94%, 95%, 96%, 97%, 98%, or 99%) identical to that of the $V_H$ of HL1 and HL2 (precursor and mature form; SEQ ID NO:6 and SEQ ID NO:8, respectively) and a $V_L$ chain that has an amino acid sequence at least 85% (e.g., 90%, 92%, 94%, 95%, 96%, 97%, 98%, or 99%) identical to that of the $V_L$ of HL2 (precursor and mature form; SEQ ID NO:10 and SEQ ID NO:12, respectively). These variants are capable of binding to an IL-20 molecule, particularly a human IL-20 molecule. In some examples, the variants possess similar antigen-binding affinity relative to the exemplary humanized antibody described above (e.g., having a $K_d < 4 \times 10^{-9}$).

(b) Anti-IL-20R Antibodies

An anti-IL-20R antibody is an antibody capable of binding to an IL-20R (e.g., binding to either one of its two subunits or binding to the dimeric complex) and inhibits the biological activity of the IL-20R and/or its downstream pathway(s) mediated by IL-20. In some examples, an anti-IL-20 antibody used in the methods described herein suppresses the IL-20 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. In some examples, the anti-IL-20R antibody specifically binds IL-20R1, such as human IL-20R1. Such an antibody may have low affinity to IL-20R2 or the IL-20R1/IL-20R2 complex or does not bind IL-20R2 or the IL-20R1/IL-20R2 complex. In other examples, the anti-IL-20R antibody specifically binds IL-20R2, such as human IL-20R2. Such an antibody may have low affinity to IL-20R1 or the IL-20R1/IL-20R2 complex or does not bind IL-20R1 or the IL-20R1/IL-20R2 complex. In yet other examples, the anti-IL-20R antibody described herein specifically binds the IL-20R1/IL-20R2 complex.

The binding affinity of an anti-IL-20R antibody to IL-20R or a subunit thereof (such as human IL-20R or human IL-20R1) can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to IL-20R is by measuring binding affinity of monofunctional Fab fragments of the antibody. To obtain monofunctional Fab fragments, an antibody (for example, IgG) can be cleaved with papain or expressed recombinantly. The affinity of an anti-IL-20R Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human IL-20R or a subunit thereof (e.g., human IL-20R1), and does not significantly bind an IL-20R from another mammalian species. In some embodiments, the antibody binds human IL-20R as well as one or more IL-20R from another mammalian species. In still other embodiments, the antibody binds IL-20R and does not significantly cross-react with other cytokine receptors. The epitope(s) bound by the antibody can be continuous or discontinuous.

In some embodiments, the antibody used in the methods described herein is an antibody having the same heavy chain and light chain variable regions ($V_H$ and $V_L$) as those of monoclonal antibody mAb7GW or mAb51D, the monoclonal antibodies, an antigen-binding fragment thereof, or a functional equivalent of either mAb7GW or mAb51D. US2011/0256093, which is herein incorporated by reference in its entirety. Shown below are the amino acid sequences of the heavy chains and light chains of mAb7GW and mAb51D, as well as their encoding nucleotide sequences.

Heavy Chain of mAb7GW:
Amino Acid Sequence
(SEQ ID NO: 14)
<u>M R V L I L L W L F T A F P G I L S</u> V V Q L Q E S
Signal peptide

G P G L V K P S Q S L S L T C T V T G Y S I T S D

Y A W N W I R Q F P G N R L E W M G Y I D Y S G S
  CDR1                                        CDR2

T K Y N P S L K S R I S V T R D T S K N Q F F L Q

L N S V T T E D T A T Y Y C A R D F G D A Y W G Q
                                         CDR3

G T L V T V S A A K T T P P S V Y P L A P G S A A

Q T N S M V T L G C L V K G Y F P E P V T V T W N

S G S L S S G V H T F P A V L Q S D L Y T L S S S

V T V P S S T W P S E T V T C N V A H P A S S T K

V D K K I V P R D C G C K P C I C T V P E V S S V

F I F P P K P K D V L T I T L T P K V T C V V V D

I S K D D P E V Q F S W F V D D V E V H T A Q T Q

P R E E Q F N S T F R S V S E L P I M H Q D W L N

G K E F K C R V N S A A F P A P I E K T I S K T K

G R P K A P Q V Y T I P P P K E Q M A K D K V S L

T C M I T D F F P E D I T V E W Q W N G Q P A E N

Y K N T Q P I M D T D G S Y F V Y S K L N V Q K S

*N W E A G N T F T C S V L H E G L H N H H T E K S*

*L S H S P G K*
(The italic region refers to the heavy chain constant region.)

Nucleotide Sequence
(SEQ ID NO: 15)
<u>ATGAGAGTGCTGATTCTTTTGTGGCTGTTCACAGCCTTTCCTGGTATCCT</u>
    Signal peptide <u>GTCT</u>GTTGTGCAGCTTCAGGAGTCGGGACCTGGCCTGGTGAAACCTTCTC AGTCTCTGTCCCTCACCTGCACTGTCACTGGCTACTCAATCACCAGTGAT
                                                          CDR1

TATGCCTGGAACTGGATCCGGCAGTTTCCAGGAAACAGACTGGAGTGGAT

GGGCTACATAGACTACAGTGGTAGCACTAAATACAACCCCTCTCTCAAAA
                           CDR2

GTCGAATCTCTGTCACTCGAGACACATCCAAGAACCAGTTCTTCCTGCAG

TTGAATTCTGTGACTACTGAGGACACAGCCACATATTACTGTGCAAGAGA

CTTTGGTGATGCTTACTGGGGCCAGGGGACTCTGGTCACTGTCTCTGCAG
   CDR3

*CCAAAACGACACCCCCATCTGTCTATCCACTGGCCCCTGGATCTGCTGCC*

*CAAACTAACTCCATGGTGACCCTGGGATGCCTGGTCAAGGGCTATTTCCC*

*TGAGCCAGTGACAGTGACCTGGAACTCTGGATCCCTGTCCAGCGGTGTGC*

*ACACCTTCCCAGCTGTCCTGCAGTCTGACCTCTACACTCTGAGCAGCTCA*

*GTGACTGTCCCCTCCAGCACCTGGCCCAGCGAGACCGTCACCTGCAACGT*

*TGCCCACCCGGCCAGCAGCACCAAGGTGGACAAGAAAATTGTGCCCAGGG*

*ATTGTGGTTGTAAGCCTTGCATATGTACAGTCCCAGAAGTATCATCTGTC*

*TTCATCTTCCCCCCAAAGCCCAAGGATGTGCTCACCATTACTCTGACTCC*

*TAAGGTCACGTGTGTTGTGGTAGACATCAGCAAGGATGATCCCGAGGTCC*

*AGTTCAGCTGGTTTGTAGATGATGTGGAGGTGCACACAGCTCAAACGCAA*

*CCCCGGGAGGAGCAGTTCAACAGCACTTTCCGCTCAGTCAGTGAACTTCC*

*CATCATGCACCAGGACTGGCTCAATGGCAAGGAGTTCAAATGCAGGGTCA*

*ACAGTGCAGCTTTCCCTGCCCCCATCGAGAAAACCATCTCCAAAACCAAA*

*GGCAGACCGAAGGCTCCACAGGTGTACACCATTCCACCTCCCAAGGAGCA*

*AATGGCCAAGGATAAAGTCAGTCTGACCTGCATGATAACAGACTTCTTCC*

*CTGAAGACATTACTGTGGAGTGGCAGTGGAATGGGCAGCCAGCGGAGAAC*

*TACAAGAACACTCAGCCCATCATGGACACAGATGGCTCTTACTTCGTCTA*

*CAGCAAGCTCAATGTGCAGAAGAGCAACTGGGAGGCAGGAAATACTTTCA*

*CCTGCTCTGTGTTACATGAGGGCCTGCACAACCACCATACTGAAGAGC*

*CTCTCCCACTCTCCTGGTAAATGA*
(The italic region encodes the heavy chain constant region.)

Light Chain of mAb7GW:
Amino Acid Sequence
(SEQ ID NO: 16)
<u>M D S Q A Q V L M L L L L W V S G S C</u> G D I V M S
        Signal peptide Q S P S S L A V S V G E K V T M S C K S S Q S L L
                                                            CDR1

Y S R N Q K N Y L A W Y Q L K P G Q S P K L L I Y

W A S T R E S G V P D R F T G S G S G T D F T L T
   CDR2

I S S V K A E D L A V Y Y C Q Q Y Y S Y P L T F G
                                          CDR3

A G T K L E L K R A D A A P T V S I F P P S S E Q

L T S G G A S V V C F L N N F Y P K D I N V K W K

I D G S E R Q N G V L N S W T D Q D S K D S T Y S

M S S T L T L T K D E Y E R H N S Y T C E A T H K

T S T S P I V K S F N R N E C
(The italic region refers to the light chain constant region.)

Nucleotide Sequence
(SEQ ID NO: 17)
<u>ATGGATTCACAGGCCCAGGTTCTTATGTTACTGCTGCTATGGGTATCTGG</u>
         Signal peptide <u>TTCCTGTGGG</u>GACATTGTGATGTCACAGTCTCCATCCTCCCTAGCTGTGT CAGTTGGAGAGAAGGTTACTATGAGCTGCAAGTCCAGTCAGAGCCTTTTA
                                                            CDR1

TATAGTAGGAATCAAAAGAACTACTTGGCCTGGTACCAGCTGAAGCCAGG

GCAGTCTCCTAAACTGCTGATTTACTGGGCATCCACTAGGGAATCTGGGG
                                          CDR2

TCCCTGATCGCTTCACAGGCAGTGGATCTGGGACAGATTTCACTCTCACC

ATCAGCAGTGTGAAGGCTGAAGACCTGGCAGTTTATTACTGTCAGCAATA

TTATAGCTATCCGCTCACGTTCGGTGCTGGGACCAAGCTGGAGCTGAAAC

*GGGCTGATGCTGCACCAACTGTATCCATCTTCCCACCATCCAGTGAGCAG*

*TTAACATCTGGAGGTGCCTCAGTCGTGTGCTTCTTGAACAACTTCTACCC*

*CAAAGACATCAATGTCAAGTGGAAGATTGATGGCAGTGAACGACAAAATG*

*GCGTCCTGAACAGTTGGACTGATCAGGACAGCAAAGACAGCACCTACAGC*

*ATGAGCAGCACCCTCACGTTGACCAAGGACGAGTATGAACGACATAACAG*

*CTATACCTGTGAGGCACTCACAAGACATCAACTTCACCCATTGTCAAGA*

*GCTTCAACAGGAATGAGTGTTAG*
(The italic region encodes the light chain constant region.)

Heavy Chain of mAb51D:
Amino Acid Sequence
(SEQ ID NO: 18)
<u>M N F G L S L I F L A L I L K G V Q C</u> E V Q L V E A G G D L V K P G G S L K L S C A A S G F S L S N
    Signal peptide

Y G M S W V R Q T P D K R L E W V A S I S S G G R F T S Y P D S V R G R F T I S R D N A K N T L Y L
CDR1                                  CDR2

QMSGLKSEDTAMYYCARHDGNGGDYWGQGTSVTVSS*AKTTPPSVYPLAPG*
                                  CDR3

*SAAQTNSMVTLGCLVKGYFPEPVTVTWNSGSLSSGVHTFPAVLQSDLYTL*

*SSSVTVPSSTWPSETVTCNVAHPASSTKVDKKIVPRDCGCKPCICTVPEV*

*SSVFIFPPKPKDVLTITLTPKVTCVVVDISKDDPEVQFSWFVDDVEVHTA*

*QTQPREEQFNSTFRSVSELPIMHQDWLNGKEFKCRVNSAAFPAPIEKTIS*

*KTKGRPKAPQVYTIPPPKEQMAKDKVSLTCMITDFFPEDITVEWQWNGQP*

*AENYKNTQPIMDTDGSYFVYSKLNVQKSNWEAGNTFTCSVLHEGLHNHHT*

-continued

EKSLSHSPGK
(The italic region refers to the heavy chain constant region.)

Nucleotide Sequence
(SEQ ID NO: 19)
ATGAACTTCGGGCTCAGCCTGATTTTCCTTGCCCTCATTTTAAAAGGTGT
Signal peptide

CCAGTGTGAGGTGCAGCTGGTGGAGGCTGGGGGAGACTTAGTGAAGCCTG

GAGGGTCCCTGAAACTCTCCTGTGCGGCCTCTGGATTCAGTTTGAGTAAC

TATGGCATGTCCTGGGTTCGCCAGACTCCAGACAAGAGGCTGGAGTGGGT
CDR1

CGCAAGCATTAGTAGTGGTGGTCGTTTCACCTCCTATCCAGACAGTGTGA
CDR2

GGGGGCGATTCACCATCTCCAGAGACAATGCCAAGAACACCCTGTACCTG

CAAATGAGCGGTCTGAAGTCTGAGGACACAGCCATGTATTACTGTGCAAG

ACACGACGGCAACGGTGGGGACTACTGGGGTCAAGGAACCTCAGTCACCG
CDR3

TCTCCTCAGCCAAAACGACACCCCCATCTGTCTATCCACTGGCCCCTGGA

*TCTGCTGCCCAAACTAACTCCATGGTGACCCTGGGATGCCTGGTCAAGGG*

*CTATTTCCCTGAGCCAGTGACAGTGACCTGGAACTCTGGATCCCTGTCCA*

*GCGGTGTGCACACCTTCCCAGCTGTCCTGCAGTCTGACCTCTACACTCTG*

*AGCAGCTCAGTGACTGTCCCCTCCAGCACCTGGCCCAGCGAGACCGTCAC*

*CTGCAACGTTGCCCACCCGGCCAGCAGCACCAAGGTGGACAAGAAAATTG*

*TGCCCAGGGATTGTGGTTGTAAGCCTTGCATATGTACAGTCCCAGAAGTA*

*TCATCTGTCTTCATCTTCCCCCCAAAGCCCAAGGATGTGCTCACCATTAC*

*TCTGACTCCTAAGGTCACGTGTGTTGTGGTAGACATCAGCAAGGATGATC*

*CCGAGGTCCAGTTCAGCTGGTTTGTAGATGATGTGGAGGTGCACACAGCT*

*CAGACGCAACCCCGGGAGGAGCAGTTCAACAGCACTTTCCGCTCAGTCAG*

*TGAACTTCCCATCATGCACCAGGACTGGCTCAATGGCAAGGAGTTCAAAT*

*GCAGGGTCAACAGTGCAGCTTTCCCTGCCCCCATCGAGAAAACCATCTCC*

*AAAACCAAAGGCAGACCGAAGGCTCCACAGGTGTACACCATTCCACCTCC*

*CAAGGAGCAGATGGCCAAGGATAAAGTCAGTCTGACCTGCATGATAACAG*

*ACTTCTTCCCTGAAGCATTACTGTGGAGTGGCAGTGGAATGGGCAGCCA*

*GCGGAGAACTACAAGAACACTCAGCCCATCATGGACACAGATGGCTCTTA*

*CTTCGTCTACAGCAAGCTCAATGTGCAGAAGAGCAACTGGGAGGCAGGAA*

*ATACTTTCACCTGCTCTGTGTTACATGAGGGCCTGCACAACCACCATACT*

*GAGAAGAGCCTCTCCCACTCTCCTGGTAAATGA*
(The italic region encodes the heavy chain constant region.)

Light Chain of mAb51D:
Amino Acid Sequence
(SEQ ID NO: 20)
MDFQVQIFSFLLISASVIMSRGQIVLSQFPAILSASPGEKVTMTCRARSS
Signal peptide                                    CDR1

VSFMHWYQQKPGSSPKPWIYATSNLASGVPPRFSGSGSGTSYSLTISRVE
      CDR2

AEDAATYYCQQWSSNPYTFGGGTKLEIKR*ADAAPTVSIFPPSSEQLTSGG*
         CDR3

*ASVVCFLNNFYPKDINVKWKIDGSERQNGVLNSWTDQDSKDSTYSMSSTL*

*TLTKDEYERHNSYTCEATHKTSTSPIVKSFNRNEC*
(The italic region refers to the light chain constant region)

Nucleotide Sequence
(SEQ ID NO: 21)
ATGGATTTTCAAGTGCAGATTTTCAGCTTCCTGCTAATCAGTGCTTCAGT
Signal peptide

CATAATGTCCAGAGGACAAATTGTTCTCTCCCAGTTTCCAGCAATCCTGT

CTGCATCTCCAGGGGAGAAGGTCACAATGACTTGCAGGGCCAGGTCAAGT
CDR1

GTAAGTTTCATGCACTGGTACCAGCAGAAGCCAGGATCCTCCCCCAAACC

CTGGATTTATGCCACATCCAACCTGGCTTCTGGAGTCCCTCCTCGCTTCA
CDR2

GTGGCAGTGGGTCTGGGACCTCTTACTCTCTCACAATCAGCAGAGTGGAG

GCTGAAGATGCTGCCACTTATTACTGCCAGCAGTGGAGTAGTAACCCATA
CDR3

CACGTTCGGAGGGGGGACTAAGCTGGAAATAAAACGGGCTGATGCTGCAC

*CAACTGTATCCATCTTCCCACCATCCAGTGAGCAGTTAACATCTGGAGGT*

*GCCTCAGTCGTGTGCTTCTTGAACAACTTCTACCCCAAAGACATCAATGT*

*CAAGTGGAAGATTGATGGCAGTGAACGACAAAATGGCGTCCTGAACAGTT*

*GGACTGATCAGGACAGCAAAGACAGCACCTACAGCATGAGCAGCACCCTC*

*ACGTTGACCAAGGACGAGTATGAACGACATAACAGCTATACCTGTGAGGC*

*CACTCACAAGACATCAACTTCACCCATTGTCAAGAGCTTCAACAGGAATG*

*AGTGTTAG*
(The italic region encodes the light chain constant region.)

A functional equivalent of mAb7GW or mAb51D has the same epitope-binding specificity as mAb7GW or mAb51D and exhibits at least 20% (e.g., 30%, 40%, 50%, 60%, 70%, 80%, 90%, or greater) of the activity of neutralizing a signaling pathway mediated by IL-20R1 as relative to mAb7GW or mAb51D. In some embodiments, a functional equivalent of mAb7GW or mAb51D contains the same regions/residues responsible for antigen-binding as mAb7GW or mAb51D, such as the same specificity-determining residues in the CDRs or the whole CDRs. The regions/residues that are responsible for antigen-binding can be identified from amino acid sequences of the heavy chain/light chain sequences of mAb7GW or mAb51D (shown above) by methods known in the art. See, e.g., www.bioinf.org.uk/abs; Almagro, J. Mol. Recognit. 17:132-143 (2004); and Chothia et al., J. Mol. Biol. 227:799-817 (1987).

In some examples, a functional equivalent (variant) of mAb7GW or mAb51D comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of mAb7GW or mAb51D, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of mAb7GW or mAb51D.

Alternatively, the functional equivalent of mAb7GW or mAb51D comprises a $V_H$ chain at least 75% (e.g., 80%, 85%, 90%, 95%, or 98%) identical to the $V_H$ chain (mature or precursor) of mAb7GW or mAb51D and a $V_L$ chain at least 75% (e.g., 80%, 85%, 90%, 95%, or 98%) identical to the $V_L$ chain (mature of precursor) of mAb7GW or mAb51D.

In other examples, a functional equivalent of mAb7GW or mAb51D comprises a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of mAb7GW or mAb51D, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of mAb7GW or mAb51D.

(c) Antibody Preparation

Antibodies capable of interfering with the IL-20 signaling pathway as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., human IL-20 or IL-20R1) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-IL-20 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the IL-20 signaling pathway. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the signaling pathway mediated by IL-20. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Methods for constructing humanized antibodies are also well known in the art. See, e.g., Queen et al., *Proc. Natl. Acad. Sci. USA*, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to IL-20R1 or IL-20R2 can be identified from the library following routine procedures. Positive clones can be subjected to further screening to identify those that suppress IL-20 receptor activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the IL-20 polypeptide have been replaced (swapped) with sequences from a closely related, but antigenically distinct protein (such as another member of the neurotrophin protein family). By assessing binding of the antibody to the mutant IL-20, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Other IL-20 Antagonists

IL-20 antagonists other than antibodies capable of interfering with the IL-20 signaling pathway as described above can be used in the methods described herein.

In some embodiments of the invention, the IL-20 antagonist comprises at least one antisense nucleic acid molecule capable of blocking or decreasing the expression of a functional IL-20 (e.g., a human IL-20) or a subunit of an IL-20 receptor (e.g., IL-20R1). Nucleotide sequences of the IL-20 and IL-20 receptor subunits are known and are readily available from publicly available databases. See above disclosures. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-0 sugar modifications well known in the art.

Alternatively, IL-20/IL-20R expression and/or release can be decreased using gene knockdown, morpholino oligonucleotides, small interfering RNA (siRNA or RNAi), microRNA or ribozymes, methods that are well-known in the art. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. Alternatively, it can be a microRNA.

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

In other embodiments, the IL-20 antagonist comprises at least one IL-20 or IL-20R inhibitory compound. As used herein, "IL-20 inhibitory compound" or "IL-20R inhibitory compound" refers to a compound other than an anti-IL-20 or anti-IL-20R antibody that directly or indirectly reduces, inhibits, neutralizes, or abolishes IL-20/IL-20R biological activity. An IL-20/IL-20R inhibitory compound should exhibit any one or more of the following characteristics: (a) binds to IL-20 or IL-20R and inhibits its biological activity and/or downstream pathways mediated by IL-20 signaling function; (b) prevents, ameliorates, or treats any aspect of neural injury, e.g., spinal cord injury (SCI); (c) blocks or decreases IL-20 receptor activation; (d) increases clearance of IL-20 or IL-20R; (e) inhibits (reduces) IL-20 or IL-20R synthesis, production or release. One skilled in the art can prepare other small molecules inhibitory compounds.

In some embodiments, an IL-20 or IL-20R inhibitory compound is an IL-20 mutant, an IL-19 mutant, or an IL-24 mutant, which can bind to an IL-20 receptor but cannot elicit signal transduction. Such a mutant may block binding of wild type IL-20 to an IL-20 receptor thus preventing IL-20 signal transduction.

In other embodiments, the IL-20 or IL-20R inhibitory compounds described herein are small molecules, which can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the IL-20-antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al., *J. Med. Chem.* 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

In other embodiments, the IL-20 antagonists can be a polypeptide comprising an extracellular portion of an IL-20 receptor (such as IL-20 R1, IL-20R2, or IL-22R1), wherein the polypeptide specifically binds to 11-20 and blocks its interaction with one or more IL-20 receptors. In some embodiments, the extracellular portion of the IL-20 receptor is fused to a Fc domain of antibody. Examples of the soluble receptors are described in PCT WO 01/46232.

Identification of IL-20 Antagonists

IL-20 antagonists can be identified or characterized using methods known in the art, whereby reduction, amelioration, or neutralization of an IL-20 biological activity is detected and/or measured. For example, an ELISA-type assay may be suitable for qualitative or quantitative measurement of IL-20 mediated kinase activation by measuring the phosphorylation of proteins activated through an IL-20 cascade. Examples include JNK, ERK, AKT, p38, STAT3 and TRAF6.

The IL-20 antagonists can also be identified by incubating a candidate agent with IL-20 or IL-20R and monitoring any one or more of the following characteristics: (a) binding to IL-20 or IL-20R and inhibiting its biological activity and/or downstream pathways mediated by IL-20 signaling function; (b) preventing, ameliorating, or treating any aspect of neural injury, e.g., spinal cord injury (SCI); (c) blocking or decreasing IL-20 receptor activation; (d) increasing clearance of IL-20 or IL-20R; (e) inhibiting (reducing) IL-20 synthesis, production or release. In some embodiments, an IL-20 antagonist is identified by incubating a candidate agent with IL-20 or IL-20R and monitoring binding and attendant reduction or neutralization of a biological activity of IL-20 or IL-20R. The binding assay may be performed with purified IL-20 or IL-20R polypeptide(s), or with cells naturally expressing, or transfected to express, IL-20 or IL-20R polypeptide(s). In one embodiment, the binding assay is a competitive binding assay, where the ability of a candidate antibody to compete with a known IL-20 antagonist for IL-20 or IL-20R binding is evaluated. The assay may be performed in various formats, including the ELISA format. In other embodiments, an IL-20 antagonist is identified by incubating a candidate agent with IL-20 or IL-20R (e.g., IL-20R1) and monitoring attendant inhibition of IL-20R1/IL-20R2 complex formation or IL-20R2/IL-22R1 complex formation. Following initial identification, the activity of a candidate IL-20 antagonist can be further confirmed and refined by bioassays, known to test the targeted biological activities. Alternatively, bioassays can be used to screen candidates directly.

The examples provided below provide a number of assays that can be used to screen candidate IL-20 antagonists. Bioassays include but are not limited to flow cytometry of determine competitive binding of IL-20 to cells in the presence of candidate IL-20 antagonists; and inhibition of IL-20-induced apoptosis in renal epithelial cells. In addition, RT-PCR or Real-time PCR which can be used to directly measure IL-20 expression or to measure expression of genes upregulated by IL-20 such as TNFα, MCP-1, IL-1β, IL-6 and VEGF.

Pharmaceutical Compositions

One or more of the above-described IL-20 antagonist can be mixed with a pharmaceutically acceptable carrier (excipient), including buffer, to form a pharmaceutical composition for use in alleviating neural injury, e.g., spinal cord injury (SCI). "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. In one example, a pharmaceutical composition described herein contains more than one anti-IL-20 or anti-IL-20R antibodies that recognize different epitopes of the target antigen. In another example, the pharmaceutical composition comprises at least two different-typed IL-20 antagonists (e.g., one antibody and one small molecule).

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the IL-20 antagonist (such as an antibody), which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S.

Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., an IL-20 antagonist) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(v nyl-alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPO™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g., Span 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing an IL-20 antagonist with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Use of IL-20 Antagonists for Alleviating Neural Injury

To practice the method disclosed herein, an effective amount of the pharmaceutical composition described above can be administered to a subject (e.g., a human subject) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, IL-20 antagonists can be aerosolized using a fluorocarbon formulation and a metered dose inhaler, or inhaled as a lyophilized and milled powder.

"Neural injury," as used herein, refers to injury to any neural tissue, including neural tissues in the central neural system (CNS) and neural tissues in the peripheral neural system (PNS), due to any causes, such as neurosurgery, trauma, ischemia, hypoxia, neurodegenerative disease (e.g., Parkinson's disease, or Alzheimer's disease), a demyelinating disease (e.g., multiple sclerosis), metabolic disorder, infectious disease, compression of the intervertebral disc, tumors, or other disorders or conditions that involve neuronal cell death or dysfunction. Neural injuries include those affecting the central nervous system (e.g., trauma to the brain and/or spinal cord), the peripheral nervous system (e.g., trauma to peripheral nerves, peripheral neuropathy), or both. In some embodiments, the methods described herein aims at treating spinal cord injury (SCI). In other examples, the methods described herein are for treating traumatic brain injury (TBI), peripheral neuropathy, or alleviating neural injury associated with a disease or disorder (e.g., a neurodegenerative disease).

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having neural injury such as SCI.

A human patient (subject) having neural injury such as SCI can have symptoms that vary widely, from pain to paralysis to incontinence. A human patient suspected of having neural injury (e.g., SCI) might be asymptomatic or show one or more symptoms associated with the neural injury, such as loss of movement, loss of sensation (including the ability to feel heat, cold and touch), loss of bowel or bladder control, exaggerated reflex activities or spasms, changes in sexual function, sexual sensitivity and fertility, pain or an intense stinging sensation caused by damage to the nerve fibers in the spinal cord, and difficulty breathing, coughing or clearing secretions from the lungs. Such subjects may be identified via routine medical procedures. A human patient at risk for neural injury such as SCI may exhibit one or more risk factors associated with an increased risk of the injury.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, any disease and disorders associated with neural injury or neurological disorders, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of neural injury, e.g., SCI. Alternatively, sustained continuous release formulations of an IL-20 antagonist may be appropriate. Various formulations and devices for achieving sustained release are known in the art.

In one example, dosages for an IL-20 antagonist as described herein may be determined empirically in individuals who have been given one or more administration(s) of IL-20 antagonist. Individuals are given incremental dosages of the antagonist. To assess efficacy of the antagonist, an indicator of reduction of symptoms of neural injury, e.g., SCI, such as improved motor performance, can be followed.

Generally, for administration of any of the antibodies described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate neural injury (e.g., SCI), or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

When the IL-20 antagonist is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an IL-20 antagonist will depend on the specific IL-20 antagonist(s) (or compositions thereof) employed, the type and severity of neural injury, whether the antagonist is administered for preventive or therapeutic purposes, previous therapy, the patient's clinical history and response to the antagonist, and the discretion of the attending physician. Typically the clinician will administer an IL-20 antagonist, such as an anti-IL-20 or anti-IL-20R antibody, until a dosage is reached that achieves the desired result. Administration of an IL-20 antagonist can be continuous or intermittent, depending, for example, upon the recipient's physiological condition, whether the purpose of the administration is therapeutic or prophylactic, and other factors known to skilled practitioners. The administration of an IL-20 antagonist (for example if the IL-20 antagonist is an anti-IL-20 antibody) may be essentially continuous over a preselected period of time or may be in a series of spaced dose, e.g., either before, during, or after developing a neural injury, for example SCI.

As used herein, the term "alleviating" refers to the application or administration of a composition including one or more active agents to a subject, who has a neural injury (e.g., SCI), a symptom of the neural injury, or a predisposition toward the neural injury, with the purpose to cure, heal, relieve, alter, remedy, ameliorate, improve, or affect the neural injury or disorder, the symptoms of such, or the predisposition toward a neural injury or disorder.

Alleviating neural injury includes delaying the development or progression of the symptoms of neural injury, reducing severity of the symptoms, or reducing the risk for developing neural injury. Alleviating the neural injury, e.g., SCI, does not necessarily require curative results. As used therein, "delaying" the development of a neural injury (such as SCI) means to defer, hinder, slow, retard, stabilize, and/or postpone progression of the injury or disorder, or its symptoms. This delay can be of varying lengths of time, depending on the history of the neural injury and/or individuals being treated. A method that "delays" or alleviates the development of a neural injury, or delays the onset of the neural injury, is a method that reduces probability of developing one or more symptoms of the neural injury or disorder in a given time frame and/or reduces extent of the symptoms in a given time frame, when compared to not using the method. Such comparisons are typically based on clinical studies, using a number of subjects sufficient to give a statistically significant result.

"Development" or "progression" of a neural injury (e.g., SCI) means initial manifestations and/or ensuing progression of the neural injury, or symptoms thereof. Development of the neural injury can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of neural injury includes initial onset and/or recurrence.

In some embodiments, the IL-20 antagonist (e.g., an anti-IL-20 antibody or anti-IL-20R antibody such as anti-IL-20R1 antibody) described herein is administered to a subject in need of the treatment at an amount sufficient to reduce the level of the IL-20 receptor/IL-20-mediated signaling by at least 20% (e.g., 30%, 40%, 50%, 60%, 70%, 80%, 90% or greater). In other embodiments, the amount of an IL-20 antagonist (e.g., an anti-IL-20 antibody or an anti-IL-20R1 antibody) used in the methods described herein is effective in improving symptoms of neural injury (e.g., SCI), such as improving motor performance of the subject. In yet other embodiments, the amount of the IL-20 antagonist is effective in maintaining the present neurological condition or suppressing the development of further neurological deficits (for example maintaining current motor performance of the subject or suppressing further loss of motor performance of the subject).

Conventional methods, known to those of ordinary skill in the art of medicine, can be used to administer the pharmaceutical composition to the subject, depending upon the type of neural injury or disorder to be treated or the site of the neural injury. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the protein-based IL-20 antagonists described herein (e.g., anti-IL-20 antibody, or anti-IL-20R antibody). For example, other IL-20 receptor fragments that are capable of blocking (from partial to complete blocking) IL-20 and/or an IL-20 biological activity are known in the art.

The particular dosage regimen, i.e., dose, timing and repetition, used in the method described herein will depend on the particular subject and that subject's medical history.

In some embodiments, more than one IL-20 antagonist, such as an antibody and a small molecule IL-20 inhibitory compound, may be administered to a subject in need of the treatment. The antagonist can be the same type or different from each other. At least one, at least two, at least three, at least four, at least five different IL-20 antagonists can be co-administered. Generally, those IL-20 antagonists have complementary activities that do not adversely affect each other. IL-20 antagonists can also be used in conjunction with other agents that serve to enhance and/or complement the effectiveness of the agents.

Treatment efficacy can be assessed by methods well-known in the art, e.g., those described in the Example below.

Kits For Use in Alleviating Neural Injury

The present disclosure also provides kits for use in alleviating neural injury, such as SCI. Such kits can include one or more containers comprising an IL-20 antagonist (such as an antibody, e.g., mAb7E or its functional variant, mAb7GW or its functional variant, or mAb51D or its functional variant). In some embodiments, the IL-20 antagonist is any antibody capable of interfering with the IL-20 signaling pathway as described herein. In other embodiments, the kit comprises an IL-20 antagonist that is other than the just-noted antibody.

In some embodiments, the kit can comprise instructions for use in accordance with any of the methods described herein. The included instructions can comprise a description of administration of the IL-20 antagonist to treat, delay the onset, or alleviate neural injury according to any of the methods described herein. The kit may further comprise a description of selecting an individual suitable for treatment based on identifying whether that individual has neural injury. In still other embodiments, the instructions comprise a description of administering an IL-20 antagonist to an individual at risk of neural injury (e.g., SCI), or developing symptoms of such.

The instructions relating to the use of an IL-20 antagonist generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating neural injury. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an IL-20 antagonist, such as an anti-IL-20 antibody.

Kits may optionally provide additional components such as buffers and interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

IL-20 Antagonists Improve Functional Outcome of Contusive Spinal Cord Injury

Rats having contusive spinal cord injury (SCI) were treated with an anti-IL-20 antibody or a saline control to examine whether blocking the IL-20 activity would be effective in treating spinal cord injury as follows.

Contusive SCI was induced in rats following the method described in Lee et al., *Spine*, January 1; 37(1):10-7, 2012 with modifications. In particular, a weighted rod was dropped onto the exposed dura of the spinal cord from 25 mm as opposed to 50 mm described in Lee et al. The SCI rats were divided into 2 groups, one group being treated via subcutaneous injections of an anti-IL-20 antibody mAb 7E at a dosage of 10 mg/kg at 10-min, 24-hour and 48-hour (total of 3 doses) post-contusion (experimental group) and the other group being treated with saline via subcutaneous injection (control group) at the same time points. Using the Basso-Beattie-Bresnahan (BBB) scale and cortical somatosensory evoked potentials (CSEP), functional evaluations were recorded weekly.

The rats were then subjected to electrophysiological testing to determine the presence or absence of CSEPs. This testing provided a noninvasive means of assessing somatosensory system functioning.

As shown in FIG. 1, the control group ("Control") showed no detectable CSEPs following SCI. By contrast, CSEPs were observed in the SCI rats treated with the anti-IL-20 antibody ("anti-IL20"). These results indicated that blocking the IL-20 activity by an IL-20 antagonist such as an anti-IL-20 antibody can preserve the somatosensory system functioning following SCI. Thus, IL-20 antagonists are protective of somatosensory system functioning following SCI.

Next, the protective effect of IL-20 antagonists on motor performance following SCI was investigated, using the Basso-Beattie-Bresnahan (BBB) scale to assess functional recovery and locomotor testing in the severe contusive SCI rat model described above. The scale (0-21) represents sequential recovery stages and categorizes combinations of rat joint movement, hindlimb movements, stepping, forelimb and hindlimb coordination, trunk position and stability, paw placement and tail position, etc.

Figure 2:
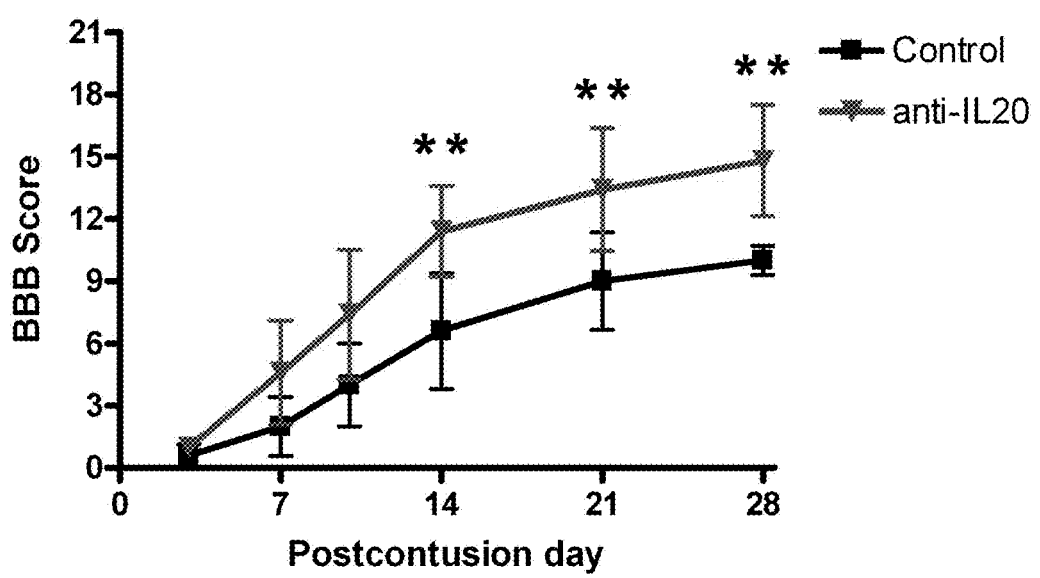
FIG. 2 is a graph showing significantly improved motor function following SCI resulting from administration of anti-IL-20 antibody mAb7E in vivo. The mean Basso-Beattie-Bresnahan (BBB) scores in animals receiving anti-IL-20 antibody treatment rose steadily from post-contusion day (PCD) 14 to PCD 28 ($P<0.05$).

As shown in FIG. 2, the SCI rats treated with anti-IL-20 antibody mAb 7E showed significantly increased improvement in BBB scores at each time point tested, as compared to the control animals ("anti-IL20" vs. "Control"). These results indicated that anti-IL-20 antagonists such as anti-IL-20 antibodies can improve motor performance following SCI.

In sum, the results from this study demonstrated that IL-20 is involved in the pathogenesis of SCI, and that antagonists of IL-20 such as anti-IL-20 antibodies can be used to alleviate symptoms of SCI.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for alleviating a neural injury in a subject, comprising administering to a subject in need thereof an effective amount of an IL-20 antagonist, wherein the neural injury is spinal cord injury (SCI), and wherein the IL-20 antagonist is an antibody that binds IL-20 or an antibody that binds an IL-20 receptor.

2. The method of claim 1, wherein the antibody is an antibody that binds human IL-20.

3. The method of claim 2, wherein the antibody that binds human IL-20 is monoclonal antibody mAb7E, an antigen-binding fragment thereof, or a functional variant thereof, wherein the functional variant of mAb7E comprises the same complementary determining regions (CDRs) as mAb7E.

4. The method of claim 3, wherein the functional variant of mAb7E is a humanized antibody of mAb7E.

5. The method of claim 4, wherein the humanized antibody comprises a heavy chain variable region ($V_H$), which comprises the amino acid sequence of SEQ ID NO:8, and a light chain variable region ($V_L$), which comprises the amino acid sequence of SEQ ID NO:12 or SEQ ID NO:13.

6. The method of claim 1, wherein the antibody is an antibody that binds a human IL-20 receptor.

7. The method of claim 6, wherein the antibody binds subunit R1 of the human IL-20 receptor (IL-20R1).

8. The method of claim 7, wherein the antibody that binds human IL-20R1 is an antibody comprising the same $V_H$ and $V_L$ chain as monoclonal antibody mAb51D or mAb7GW, or a functional variant thereof, wherein the functional variant of mAb51D comprises the same complementary determining regions (CDRs) as mAb51D and the functional variant of mAb7GW comprises the same CDRs as mAb7GW.

9. The method of claim 8, wherein the functional variant of mAb51D or mAb7GW is a humanized antibody of mAb51D or mAb7GW.

10. The method of claim 1, wherein the antibody is a full-length antibody or an antigen-binding fragment thereof.

11. The method of claim 1, wherein the antibody is a humanized antibody, a chimeric antibody, or a single-chain antibody.

12. The method of claim 1, wherein the subject is a human patient having spinal cord injury (SCI).

13. The method of claim 1, wherein the amount of the IL-20 antagonist is effective in reducing one or more symptoms associated with SCI.

14. The method of claim 13, wherein the amount of the IL-20 antagonist is effective in suppressing the loss of cortical somatosensory evoked potentials in the subject, improving motor performance of the subject, or both.

* * * * *

SEQUENCE LISTING

```
<160> NUMBER OF SEQ ID NOS: 21

<210> SEQ ID NO 1
<211> LENGTH: 363
<212> TYPE: DNA
<213> ORGANISM: Mouse

<400> SEQUENCE: 1
gaattgaagc ttgaggagtc tggaggaggc ttggtgcagc ctggaggatc catgaaactc      60
tcttgtgctg cctctggatt cactttagt gacgcctgga tggactgggt ccgccagtct     120
ccagagaagg ggcttgagtg gattgctgaa attagaagca aagctaataa ttatgcaaca     180
tactttgctg agtctgtgaa agggaggttc accatctcaa gagatgattc caaaagtggt     240
gtctacctgc aaatgaacaa cttaagagct gaggacactg gcatttattt ctgtaccaag     300
ttatcactac gttactggtt cttcgatgtc tggggcgcag ggaccacggt caccgtctcc     360
tca                                                                   363

<210> SEQ ID NO 2
<211> LENGTH: 121
<212> TYPE: PRT
<213> ORGANISM: Mouse

<400> SEQUENCE: 2

Glu Leu Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Ile
        35                  40                  45

Ala Glu Ile Arg Ser Lys Ala Asn Asn Tyr Ala Thr Tyr Phe Ala Glu
```

```
                50                  55                  60
Ser Val Lys Gly Arg Phe Thr Ile Ser Arg Asp Asp Ser Lys Ser Gly
 65                  70                  75                  80

Val Tyr Leu Gln Met Asn Asn Leu Arg Ala Glu Asp Thr Gly Ile Tyr
                 85                  90                  95

Phe Cys Thr Lys Leu Ser Leu Arg Tyr Trp Phe Phe Asp Val Trp Gly
                100                 105                 110

Ala Gly Thr Thr Val Thr Val Ser Ser
            115                 120

<210> SEQ ID NO 3
<211> LENGTH: 339
<212> TYPE: DNA
<213> ORGANISM: Mouse

<400> SEQUENCE: 3
gattttgtga tgacccagac tccactcact ttgtcggtta ccattggaca accagcctcc      60
atctcttgca agtcaagtca gagcctcttg atagtgatg aaagacata tttgaattgg      120 ttgttacaga ggccaggcca gtctccaaag cacctcatct atctggtgtc taaactggac      180
tctggagtcc ctgacaggtt cactggcagt ggatcaggga ccgatttcac actgagaatc      240
agcagagtgg aggctgagga tttgggagtt tattattgct ggcaaagtac acattttccg      300
tggacgttcg gtggaggcac caagctggaa atcaaacgg                            339

<210> SEQ ID NO 4
<211> LENGTH: 113
<212> TYPE: PRT
<213> ORGANISM: Mouse

<400> SEQUENCE: 4

Asp Phe Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
            35                  40                  45

Pro Lys His Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
 65                  70                  75                  80

Ser Arg Val Glu Ala Glu Asp Leu Gly Val Tyr Tyr Cys Trp Gln Ser
                 85                  90                  95

Thr His Phe Pro Trp Thr Phe Gly Gly Gly Thr Lys Leu Glu Ile Lys
                100                 105                 110

Arg

<210> SEQ ID NO 5
<211> LENGTH: 420
<212> TYPE: DNA
<213> ORGANISM: Artificial Sequence
<220> FEATURE:
<223> OTHER INFORMATION: Oligonucleotide

<400> SEQUENCE: 5
atgtacttgg gactgaacta tgttttcatc gttttctcc tgaatggtgt ccagagtgaa      60
gtgcagcttg tggagtctgg aggaggcttg gtgcagcctg gaggatccct gaaactctct      120
```

```
tgtgctgcct ctggattcac ttttagtgac gcctggatgg actgggtccg ccaggcttcc       180
gggaaggggc ttgagtggat tgctgaaatt agaagcaaag ctaataatta tgcaacatac       240
tttgctgagt ctgtgaaagg gaggttcacc atctcaagag atgattccaa aaacaccgcc       300
tacctgcaaa tgaacagctt aaaaaccgag acactgccg tttattactg taccaagtta       360
tcactgcgtt actggttctt cgatgtctgg ggccagggga ccctggtcac cgtctcctca       420
```

<210> SEQ ID NO 6
<211> LENGTH: 140
<212> TYPE: PRT
<213> ORGANISM: Artificial Sequence
<220> FEATURE:
<223> OTHER INFORMATION: Polypeptide

<400> SEQUENCE: 6

```
Met Tyr Leu Gly Leu Asn Tyr Val Phe Ile Val Phe Leu Leu Asn Gly
  1               5                  10                  15

Val Gln Ser Glu Val Gln Leu Val Glu Ser Gly Gly Gly Leu Val Gln
             20                  25                  30

Pro Gly Gly Ser Leu Lys Leu Ser Cys Ala Ala Ser Gly Phe Thr Phe
         35                  40                  45

Ser Asp Ala Trp Met Asp Trp Val Arg Gln Ala Ser Gly Lys Gly Leu
     50                  55                  60

Glu Trp Ile Ala Glu Ile Arg Ser Lys Ala Asn Asn Tyr Ala Thr Tyr
 65                  70                  75                  80

Phe Ala Glu Ser Val Lys Gly Arg Phe Thr Ile Ser Arg Asp Asp Ser
                 85                  90                  95

Lys Asn Thr Ala Tyr Leu Gln Met Asn Ser Leu Lys Thr Glu Asp Thr
            100                 105                 110

Ala Val Tyr Tyr Cys Thr Lys Leu Ser Leu Arg Tyr Trp Phe Phe Asp
        115                 120                 125

Val Trp Gly Gln Gly Thr Leu Val Thr Val Ser Ser
    130                 135                 140
```

<210> SEQ ID NO 7
<211> LENGTH: 363
<212> TYPE: DNA
<213> ORGANISM: Artificial Sequence
<220> FEATURE:
<223> OTHER INFORMATION: Oligonucleotide

<400> SEQUENCE: 7

```
gaagtgcagc ttgtggagtc tggaggaggc ttggtgcagc ctggaggatc cctgaaactc        60
tcttgtgctg cctctggatt cactttagt gacgcctgga tggactgggt ccgccaggct       120
tccgggaagg ggcttgagtg gattgctgaa attagaagca agctaataa ttatgcaaca       180 tactttgctg agtctgtgaa agggaggttc accatctcaa gagatgattc caaaaacacc       240
gcctacctgc aaatgaacag cttaaaaacc gaggacactg ccgtttatta ctgtaccaag       300
ttatcactgc gttactggtt cttcgatgtc tggggccagg gaccctggt caccgtctcc       360 tca                                                                    363
```

<210> SEQ ID NO 8
<211> LENGTH: 121
<212> TYPE: PRT
<213> ORGANISM: Artificial Sequence
<220> FEATURE:
<223> OTHER INFORMATION: Polypeptide

<400> SEQUENCE: 8

```
Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Asp Ala
            20                  25                  30
Trp Met Asp Trp Val Arg Gln Ala Ser Gly Lys Gly Leu Glu Trp Ile
        35                  40                  45
Ala Glu Ile Arg Ser Lys Ala Asn Asn Tyr Ala Thr Tyr Phe Ala Glu
    50                  55                  60
Ser Val Lys Gly Arg Phe Thr Ile Ser Arg Asp Asp Ser Lys Asn Thr
65                  70                  75                  80
Ala Tyr Leu Gln Met Asn Ser Leu Lys Thr Glu Asp Thr Ala Val Tyr
                85                  90                  95
Tyr Cys Thr Lys Leu Ser Leu Arg Tyr Trp Phe Phe Asp Val Trp Gly
            100                 105                 110
Gln Gly Thr Leu Val Thr Val Ser Ser
        115                 120
```

<210> SEQ ID NO 9
<211> LENGTH: 396
<212> TYPE: DNA
<213> ORGANISM: Artificial Sequence
<220> FEATURE:
<223> OTHER INFORMATION: Oligonucleotide

<400> SEQUENCE: 9

```
atgatgagtc ctgcccagtt cctgtttctg ttggtgctct ggattcggga aaccaacggt      60
gatatcgtga tgacccagac tccactctct ttgtccgtta cccctggaca accagcctcc     120
atctcttgca gtcaagtcag agcctcttgg atagtgatgg aaagacata tttgaattgg      180
ttgttacaga agccaggcca gtctccacag cacctcatct atctggtgtc taaactggac     240
tctggagtcc ctgacaggtt cagtggcagt ggatcaggga ccgatttcac actgaaaatc     300
agcagagtgg aggctgagga tgttggagtt tattattgct ggcaaagtac acatttccc     360
tggaccttcg gtggaggcac caaggtggaa atcaaa                               396
```

<210> SEQ ID NO 10
<211> LENGTH: 132
<212> TYPE: PRT
<213> ORGANISM: Artificial Sequence
<220> FEATURE:
<223> OTHER INFORMATION: Polypeptide

<400> SEQUENCE: 10

```
Met Met Ser Pro Ala Gln Phe Leu Phe Leu Leu Val Leu Trp Ile Arg
1               5                   10                  15
Glu Thr Asn Gly Asp Ile Val Met Thr Gln Thr Pro Leu Ser Leu Ser
            20                  25                  30
Val Thr Pro Gly Gln Pro Ala Ser Ile Ser Cys Lys Ser Ser Gln Ser
        35                  40                  45
Leu Leu Asp Ser Asp Gly Lys Thr Tyr Leu Asn Trp Leu Leu Gln Lys
    50                  55                  60
Pro Gly Gln Ser Pro Gln His Leu Ile Tyr Leu Val Ser Lys Leu Asp
65                  70                  75                  80
Ser Gly Val Pro Asp Arg Phe Ser Gly Ser Gly Ser Gly Thr Asp Phe
                85                  90                  95
Thr Leu Lys Ile Ser Arg Val Glu Ala Glu Asp Val Gly Val Tyr Tyr
```

```
            100                 105                 110
Cys Trp Gln Ser Thr His Phe Pro Trp Thr Phe Gly Gly Gly Thr Lys
        115                 120                 125
Val Glu Ile Lys
    130
```

<210> SEQ ID NO 11
<211> LENGTH: 336
<212> TYPE: DNA
<213> ORGANISM: Artificial Sequence
<220> FEATURE:
<223> OTHER INFORMATION: Oligonucleotide

<400> SEQUENCE: 11

```
gatatcgtga tgacccagac tccactctct ttgtccgtta cccctggaca accagcctcc      60
atctcttgca agtcaagtca gagcctcttg gatagtgatg gaaagacata tttgaattgg     120
ttgttacaga agccaggcca gtctccacag cacctcatct atctggtgtc taaactggac     180
tctggagtcc ctgacaggtt cagtggcagt ggatcaggga ccgatttcac actgaaaatc     240
agcagagtgg aggctgagga tgttggagtt tattattgct ggcaaagtac acattttccc     300
tggaccttcg gtggaggcac caaggtggaa atcaaa                              336
```

<210> SEQ ID NO 12
<211> LENGTH: 112
<212> TYPE: PRT
<213> ORGANISM: Artificial Sequence
<220> FEATURE:
<223> OTHER INFORMATION: Polypeptide

<400> SEQUENCE: 12

```
Asp Ile Val Met Thr Gln Thr Pro Leu Ser Leu Ser Val Thr Pro Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Leu Leu Gln Lys Pro Gly Gln Ser
        35                  40                  45
Pro Gln His Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Ser
                85                  90                  95
Thr His Phe Pro Trp Thr Phe Gly Gly Gly Thr Lys Val Glu Ile Lys
            100                 105                 110
```

<210> SEQ ID NO 13
<211> LENGTH: 112
<212> TYPE: PRT
<213> ORGANISM: Artificial Sequence
<220> FEATURE:
<223> OTHER INFORMATION: Polypeptide

<400> SEQUENCE: 13

```
Asp Phe Val Met Thr Gln Thr Pro Leu Ser Leu Ser Val Thr Pro Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Leu Leu Gln Lys Pro Gly Gln Ser
        35                  40                  45
```

```
Pro Gln His Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Ser
                85                  90                  95

Thr His Phe Pro Trp Thr Phe Gly Gly Gly Thr Lys Val Glu Ile Lys
            100                 105                 110
```

<210> SEQ ID NO 14
<211> LENGTH: 457
<212> TYPE: PRT
<213> ORGANISM: Mouse

<400> SEQUENCE: 14

```
Met Arg Val Leu Ile Leu Leu Trp Leu Phe Thr Ala Phe Pro Gly Ile
1               5                   10                  15

Leu Ser Val Val Gln Leu Gln Glu Ser Gly Pro Gly Leu Val Lys Pro
                20                  25                  30

Ser Gln Ser Leu Ser Leu Thr Cys Thr Val Thr Gly Tyr Ser Ile Thr
            35                  40                  45

Ser Asp Tyr Ala Trp Asn Trp Ile Arg Gln Phe Pro Gly Asn Arg Leu
    50                  55                  60

Glu Trp Met Gly Tyr Ile Asp Tyr Ser Gly Ser Thr Lys Tyr Asn Pro
65                  70                  75                  80

Ser Leu Lys Ser Arg Ile Ser Val Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Asp Phe Gly Asp Ala Tyr Trp Gly Gln Gly Thr Leu
        115                 120                 125

Val Thr Val Ser Ala Ala Lys Thr Thr Pro Pro Ser Val Tyr Pro Leu
    130                 135                 140

Ala Pro Gly Ser Ala Ala Gln Thr Asn Ser Met Val Thr Leu Gly Cys
145                 150                 155                 160

Leu Val Lys Gly Tyr Phe Pro Glu Pro Val Thr Val Thr Trp Asn Ser
                165                 170                 175

Gly Ser Leu Ser Ser Gly Val His Thr Phe Pro Ala Val Leu Gln Ser
            180                 185                 190

Asp Leu Tyr Thr Leu Ser Ser Ser Val Thr Val Pro Ser Ser Thr Trp
        195                 200                 205

Pro Ser Glu Thr Val Thr Cys Asn Val Ala His Pro Ala Ser Ser Thr
    210                 215                 220

Lys Val Asp Lys Lys Ile Val Pro Arg Asp Cys Gly Cys Lys Pro Cys
225                 230                 235                 240

Ile Cys Thr Val Pro Glu Val Ser Ser Val Phe Ile Phe Pro Pro Lys
                245                 250                 255

Pro Lys Asp Val Leu Thr Ile Thr Leu Thr Pro Lys Val Thr Cys Val
            260                 265                 270

Val Val Asp Ile Ser Lys Asp Asp Pro Glu Val Gln Phe Ser Trp Phe
        275                 280                 285

Val Asp Asp Val Glu Val His Thr Ala Gln Thr Gln Pro Arg Glu Glu
    290                 295                 300

Gln Phe Asn Ser Thr Phe Arg Ser Val Ser Glu Leu Pro Ile Met His
```

```
            305                 310                 315                 320
Gln Asp Trp Leu Asn Gly Lys Glu Phe Lys Cys Arg Val Asn Ser Ala
                325                 330                 335
Ala Phe Pro Ala Pro Ile Glu Lys Thr Ile Ser Lys Thr Lys Gly Arg
                340                 345                 350
Pro Lys Ala Pro Gln Val Tyr Thr Ile Pro Pro Lys Glu Gln Met
                355                 360                 365
Ala Lys Asp Lys Val Ser Leu Thr Cys Met Ile Thr Asp Phe Phe Pro
            370                 375                 380
Glu Asp Ile Thr Val Glu Trp Gln Trp Asn Gly Gln Pro Ala Glu Asn
385                 390                 395                 400
Tyr Lys Asn Thr Gln Pro Ile Met Asp Thr Asp Gly Ser Tyr Phe Val
                405                 410                 415
Tyr Ser Lys Leu Asn Val Gln Lys Ser Asn Trp Glu Ala Gly Asn Thr
                420                 425                 430
Phe Thr Cys Ser Val Leu His Glu Gly Leu His Asn His His Thr Glu
                435                 440                 445
Lys Ser Leu Ser His Ser Pro Gly Lys
            450                 455

<210> SEQ ID NO 15
<211> LENGTH: 1374
<212> TYPE: DNA
<213> ORGANISM: Mouse

<400> SEQUENCE: 15
atgagagtgc tgattctttt gtggctgttc acagcctttc ctggtatcct gtctgttgtg      60
cagcttcagg agtcgggacc tggcctggtg aaaccttctc agtctctgtc cctcacctgc     120
actgtcactg gctactcaat caccagtgat tatgcctgga ctggatccg gcagttccca     180 ggaaacagac tggagtggat gggctacata gactacagtg gtagcactaa atacaacccc     240
tctctcaaaa gtcgaatctc tgtcactcga gacacatcca agaaccagtt cttcctgcag     300
ttgaattctg tgactactga ggacacagcc acatattact gtgcaagaga ctttggtgat     360
gcttactggg gccaggggac tctggtcact gtctctgcag ccaaaacgac ccccatct     420 gtctatccac tggcccctgg atctgctgcc caaactaact ccatggtgac cctgggatgc     480
ctggtcaagg ctatttccc tgagccagtg acagtgacct ggaactctgg atccctgtcc     540
agcggtgtgc acaccttccc agctgtcctg cagtctgacc tctacactct gagcagctca     600
gtgactgtcc cctccagcac ctgggccagc gagaccgtca cctgcaacgt tgcccacccg     660
gccagcagca ccaaggtgga caagaaaatt gtgcccaggg attgtggttg taagccttgc     720
atatgtacag tccagaagt atcatctgtc ttcatcttcc ccccaaagcc caaggatgtg     780
ctcaccatta ctctgactcc taaggtcacg tgtgttgtgg tagacatcag caaggatgat     840
cccgaggtcc agttcagctg gtttgtagat gatgtggagg tgcacacagc tcaaacgcaa     900
ccccgggagg agcagttcaa cagcactttc cgctcagtca gtgaacttcc catcatgcac     960
caggactggc tcaatggcaa ggagttcaaa tgcagggtca acagtgcagc ttttccctgcc    1020 cccatcgaga aaaccatctc caaaaccaaa ggcagaccga aggctccaca ggtgtacacc    1080
attccacctc ccaaggagca aatggccaag ataaagtca gtctgacctg catgataaca    1140
gacttcttcc ctgaagacat tactgtggag tggcagtgga atgggcagcc agcggagaac    1200
tacaagaaca ctcagcccat catggacaca gatggctctt acttcgtcta cagcaagctc    1260
```

```
aatgtgcaga agagcaactg ggaggcagga aatactttca cctgctctgt gttacatgag    1320
ggcctgcaca accaccatac tgagaagagc ctctcccact ctcctggtaa atga          1374
```

<210> SEQ ID NO 16
<211> LENGTH: 240
<212> TYPE: PRT
<213> ORGANISM: Mouse

<400> SEQUENCE: 16

```
Met Asp Ser Gln Ala Gln Val Leu Met Leu Leu Leu Leu Trp Val Ser
1               5                   10                  15

Gly Ser Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Arg Asn Gln Lys Asn Tyr Leu Ala Trp Tyr Gln Leu
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240
```

<210> SEQ ID NO 17
<211> LENGTH: 723
<212> TYPE: DNA
<213> ORGANISM: Mouse

<400> SEQUENCE: 17

```
atggattcac aggcccaggt tcttatgtta ctgctgctat gggtatctgg ttcctgtggg     60
gacattgtga tgtcacagtc tccatcctcc ctagctgtgt cagttggaga gaaggttact    120
atgagctgca agtccagtca gagccttta tatagtagga tcaaaagaa ctacttggcc     180 tggtaccagc tgaagccagg gcagtctcct aaactgctga tttactgggc atccactagg    240
gaatctgggg tccctgatcg cttcacaggc agtggatctg ggacagattt cactctcacc    300
atcagcagtg tgaaggctga agacctggca gtttattact gtcagcaata ttatagctat    360
ccgctcacgt tcggtgctgg gaccaagctg gagctgaaac gggctgatgc tgcaccaact    420
```

```
gtatccatct tcccaccatc cagtgagcag ttaacatctg gaggtgcctc agtcgtgtgc       480
ttcttgaaca acttctaccc caaagacatc aatgtcaagt ggaagattga tggcagtgaa       540
cgacaaaatg gcgtcctgaa cagttggact gatcaggaca gcaagacag cacctacagc        600 atgagcagca ccctcacgtt gaccaaggac gagtatgaac gacataacag ctataccctgt     660 gaggccactc acaagacatc aacttcaccc attgtcaaga gcttcaacag gaatgagtgt       720
tag                                                                     723
```

<210> SEQ ID NO 18
<211> LENGTH: 460
<212> TYPE: PRT
<213> ORGANISM: Mouse

<400> SEQUENCE: 18

```
Met Asn Phe Gly Leu Ser Leu Ile Phe Leu Ala Leu Ile Leu Lys Gly
1               5                   10                  15

Val Gln Cys Glu Val Gln Leu Val Glu Ala Gly Gly Asp Leu Val Lys
            20                  25                  30

Pro Gly Gly Ser Leu Lys Leu Ser Cys Ala Ala Ser Gly Phe Ser Leu
        35                  40                  45

Ser Asn Tyr Gly Met Ser Trp Val Arg Gln Thr Pro Asp Lys Arg Leu
    50                  55                  60

Glu Trp Val Ala Ser Ile Ser Ser Gly Gly Arg Phe Thr Ser Tyr Pro
65                  70                  75                  80

Asp Ser Val Arg Gly Arg Phe Thr Ile Ser Arg Asp Asn Ala Lys Asn
                85                  90                  95

Thr Leu Tyr Leu Gln Met Ser Gly Leu Lys Ser Glu Asp Thr Ala Met
            100                 105                 110

Tyr Tyr Cys Ala Arg His Asp Gly Asn Gly Gly Asp Tyr Trp Gly Gln
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320
```

```
Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
            405                 410                 415

Tyr Phe Val Tyr Ser Lys Leu Asn Val Gln Lys Ser Asn Trp Glu Ala
        420                 425                 430

Gly Asn Thr Phe Thr Cys Ser Val Leu His Glu Gly Leu His Asn His
    435                 440                 445

His Thr Glu Lys Ser Leu Ser His Ser Pro Gly Lys
    450                 455                 460

<210> SEQ ID NO 19
<211> LENGTH: 1383
<212> TYPE: DNA
<213> ORGANISM: Mouse

<400> SEQUENCE: 19
atgaacttcg ggctcagcct gattttcctt gccctcattt taaaaggtgt ccagtgtgag      60
gtgcagctgg tggaggctgg gggagactta gtgaagcctg agggtccct gaaactctcc     120 tgtgcggcct ctggattcag tttgagtaac tatggcatgt cctgggttcg ccagactcca     180
gacaagaggc tggagtgggt cgcaagcatt agtagtggtg gtcgtttcac ctcctatcca     240
gacagtgtga gggggcgatt caccatctcc agagacaatg ccaagaacac cctgtacctg     300
caaatgagcg gtctgaagtc tgaggacaca gccatgtatt actgtgcaag acacgacggc     360
aacggtgggg actactgggg tcaaggaacc tcagtcaccg tctcctcagc caaaacgaca     420 ccccccatctg tctatccact ggcccctgga tctgctgccc aaactaactc catggtgacc     480
ctgggatgcc tggtcaaggg ctatttccct gagccagtga cagtgacctg aactctgga     540 tccctgtcca gcggtgtgca caccttccca gctgtcctgc agtctgacct ctacactctg     600
agcagctcag tgactgtccc ctccagcacc tggcccagcg accgtcac ctgcaacgtt     660 gcccacccgg ccagcagcac caaggtggac aagaaaattg tgcccaggga ttgtggttgt     720
aagccttgca tatgtacagt cccagaagta tcatctgtct tcatcttccc cccaaagccc     780
aaggatgtgc tcaccattac tctgactcct aaggtcacgt gtgttgtggt agacatcagc     840
aaggatgatc ccgaggtcca gttcagctgg tttgtagatg atgtggaggt gcacacagct     900
cagacgcaac cccgggagga gcagttcaac agcactttcc gctcagtcag tgaacttccc     960
atcatgcacc aggactggct caatggcaag gagttcaaat gcagggtcaa cagtgcagct    1020
ttccctgccc ccatcgagaa aaccatctcc aaaaccaaag cagaccgaa ggctccacag    1080 gtgtacacca ttccacctcc caaggagcag atggccaagg ataaagtcag tctgacctgc    1140
atgataacag acttcttccc tgaagacatt actgtggagt ggcagtggaa tgggcagcca    1200
gcggagaact acaagaacac tcagcccatc atggacacag atggctctta cttcgtctac    1260
agcaagctca atgtgcagaa gagcaactgg gaggcaggaa atactttcac ctgctctgtg    1320
```

```
ttacatgagg gcctgcacaa ccaccatact gagaagagcc tctcccactc tcctggtaaa    1380
tga                                                                 1383

<210> SEQ ID NO 20
<211> LENGTH: 235
<212> TYPE: PRT
<213> ORGANISM: Mouse

<400> SEQUENCE: 20

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Phe Pro Ala Ile
            20                  25                  30

Leu Ser Ala Ser Pro Gly Glu Lys Val Thr Met Thr Cys Arg Ala Arg
        35                  40                  45

Ser Ser Val Ser Phe Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Pro Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Tyr Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235

<210> SEQ ID NO 21
<211> LENGTH: 708
<212> TYPE: DNA
<213> ORGANISM: Mouse

<400> SEQUENCE: 21
atggattttc aagtgcagat tttcagcttc ctgctaatca gtgcttcagt cataatgtcc     60
agaggacaaa ttgttctctc ccagtttcca gcaatcctgt ctgcatctcc aggggagaag    120
gtcacaatga cttgcagggc caggtcaagt gtaagtttca tgcactggta ccagcagaag    180
ccaggatcct cccccaaacc ctggatttat gccacatcca acctggcttc tggagtccct    240
cctcgcttca gtggcagtgg gtctgggacc tcttactctc tcacaatcag cagagtggag    300
gctgaagatg ctgccactta ttactgccag cagtggagta gtaacccata cacgttcgga    360
ggggggacta agctggaaat aaaacgggct gatgctgcac caactgtatc catcttccca    420
```

```
ccatccagtg agcagttaac atctggaggt gcctcagtcg tgtgcttctt gaacaacttc      480 tacccccaaag acatcaatgt caagtggaag attgatggca gtgaacgaca aaatggcgtc     540
ctgaacagtt ggactgatca ggacagcaaa gacagcacct acagcatgag cagcaccctc     600
acgttgacca aggacgagta tgaacgacat aacagctata cctgtgaggc cactcacaag     660
acatcaactt cacccattgt caagagcttc aacaggaatg agtgttag                   708
```